United States Patent [19]

Fugitt et al.

[11] 4,340,606

[45] Jul. 20, 1982

[54] 3-(P-ALKYLSULFONYLPHENYL)OX-AZOLIDINONE DERIVATIVES AS ANTIBACTERIAL AGENTS

[75] Inventors: Robert B. Fugitt, Newark; Raymond W. Luckenbaugh, Wilmington, both of Del.

[73] Assignee: E. I. Du Pont de Nemours and Company, Wilmington, Del.

[21] Appl. No.: 199,698

[22] Filed: Oct. 23, 1980

[51] Int. Cl.$^3$ .................... C07D 263/38; A61K 31/42
[52] U.S. Cl. .................................... 424/272; 548/229
[58] Field of Search ........................ 548/229; 424/272

[56] References Cited

U.S. PATENT DOCUMENTS 4,128,654  12/1978  Fugitt et al. ...................... 548/229

FOREIGN PATENT DOCUMENTS 2708236  2/1977  Fed. Rep. of Germany .
2381037  9/1978  France .
2381038  9/1978  France .
2003151  3/1979  United Kingdom ................ 548/229

OTHER PUBLICATIONS

Wolff, "Burger's Medicinal Chemistry", 4th Ed., Part I, The Basis of Medicinal Chemistry, p. 170 (1980).

*Primary Examiner*—Donald G. Daus
*Assistant Examiner*—Sharon A. Gibson

[57] ABSTRACT

This invention relates to novel 3-(p-alkylsulfonylphenyl)oxazolidinone derivatives, pharmaceutical compositions containing them and methods of using them to alleviate bacterial infections in mammals.

8 Claims, No Drawings

3-(P-ALKYLSULFONYLPHENYL)OXAZOLIDINONE DERIVATIVES AS ANTIBACTERIAL AGENTS

BACKGROUND OF THE INVENTION

U.S. Pat. No. 4,128,654 to Fugitt et al. discloses, among others, compounds of the formula

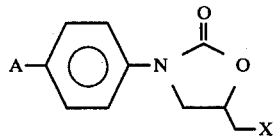

where $A=RS(O)_n$, $X=Cl$, Br, or F, $R=C_1-C_3$ alkyl and $n=0$, 1 or 2. The compounds are disclosed as being useful in controlling fungal and bacterial diseases of plants.

U.K. Pat. No. 2003-151 to Delande teaches the following compound as an antidepressant:

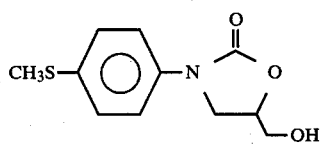

Neither reference nor any known reference suggests the novel compounds of this invention and their antibacterial activity in mammals.

SUMMARY OF THE INVENTION

It has been discovered that the novel compounds of Formula I are useful for alleviating bacterial infections in mammals:

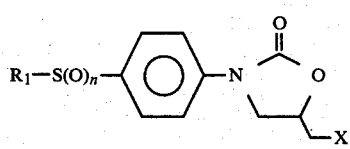  I where
$R_1 = CH_3$, $C_2H_5$, $CF_2H$, $CF_3$ or $CF_2CF_2H$;
$X =$ halogen or $OR_2$, provided that, when $R_1 = CH_3$ or $C_2H_5$, then $X = OR_2$;

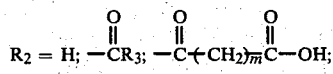

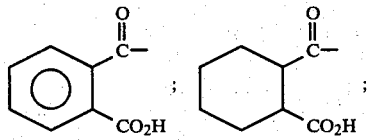

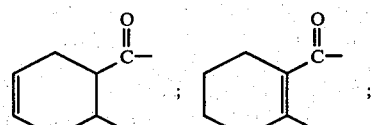

or

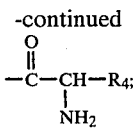

$R_3 =$ aryl or $C_1-C_{12}$ alkyl;
$R_4 =$ H, $C_1-C_5$ alkyl, $-CH_2OH$, $-CH_2SH$, aryl or aralkyl;
$n = 1$ or 2; and
$m = 2$ or 3;
and pharmaceutically acceptable acid and base salts thereof.

Preferred because of their high antibacterial activity are those compounds where, independently:
$X = OR_2$;
$R_2 = H$ or $-COR_3$; and
$n = 2$.

This invention also relates to methods of using compounds of Formula Ia to alleviate bacterial infection in mammals.

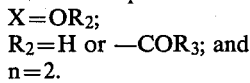 Ia where
$R_1 = CH_3$, $C_2H_5$, $CF_2H$, $CF_3$ or $CF_2CF_2H$;
$X =$ halogen or $OR_2$;

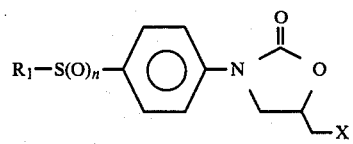

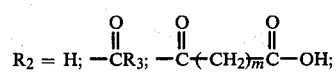

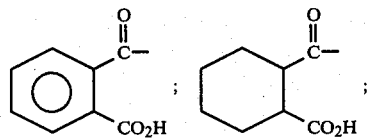

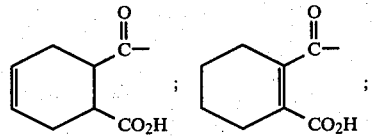

or

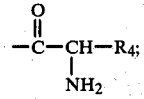

$R_3 =$ aryl or $C_1-C_{12}$ alkyl;
$R_4 =$ H, $C_1-C_5$ alkyl, $-CH_2OH$, $-CH_2SH$, aryl or aralkyl;
$n = 1$ or 2; and
$m = 2$ or 3;
and pharmaceutically acceptable acid and base salts thereof.

The term "aryl" as used in the definitions of substituents $R_3$ and $R_4$ is meant to encompass any univalent aromatic radical, either homocyclic or heterocyclic. Suitable aryl groups include radicals of monocyclic compounds such as benzene, pyridine, pyrimidine, pyrazole, furan, triazine, thiophene, imidazole, oxazole, thiazole, and pyrrole. Radicals of polycyclic compounds such as biphenyl and terphenyl as well as of condensed polycyclic compounds such as naphthalene, anthracene, phenanthrene, quinoline, isoquinoline, acridine, phenazine, indole, benzothiophene, carbazole and dibenzofuran are also suitable.

Any of the aryl groups may optionally be substituted with one or more substituents, including, but not limited to, F, Cl, Br, $NO_2$, $C_1$-$C_3$ alkyl or alkoxy, OH, $CF_3$, CN, $CO_2(C_1$-$C_3$ alkyl) or $S(O)_qCH_3$ where q=0, 1 or 2. The preferred aryl substituents are pyridine, thiophene, furan, pyrrole and benzene, optionally substituted with the above-mentioned substituents.

The term "aralkyl" used in the definition of $R_{4s}$ meant to encompass an alkyl substituent, preferably containing one to four carbon atoms, substituted with any one of the aryl substituents previously described.

DETAILED DESCRIPTION OF THE INVENTION

Synthesis:
(a) Compounds of Formula Ia where X=halogen

The halogen-substituted compounds used in the method of this invention, represented by Formulas II and III, may be prepared by the process illustrated in Scheme A:

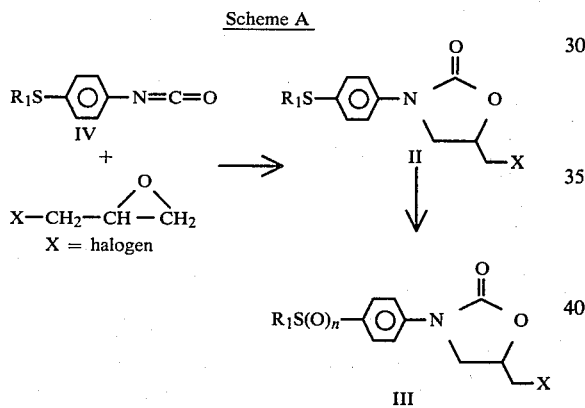

The oxazolidinonemethyl halide of Formula II can be prepared by the reaction of the appropriate isocyanate and epihalohydrin as taught in U.S. Pat. No. 4,128,654, the disclosure of which is herein incorporated by reference. It has been found that improved yields and ease of isolation of the product can be obtained by using xylene as solvent and lithium bromide-tri-n-butylphosphine oxide complex as catalyst. The reaction is carried out at a temperature in the range of about 100°-145° C., preferably about 140°-145° C.

The oxazolidinonemethyl halide of Formula II can be oxidized to yield the corresponding sulfoxide (n=1) or sulfone (n=2) of Formula III by reaction with peracids, for example m-chloroperbenzoic acid or peracetic acid. The reaction is best carried out at a temperature in the range of about 10°-60° C., preferably 20°-30° C., in a solvent such as methylene chloride or chloroform. The product can be isolated by triturating the reaction mixture with ether and filtering off the solid product. It can be further purified, if necessary, by recrystallization from a suitable solvent.

The isocyanate IV used in Scheme A is commercially available when $R_1$=$CH_3$ or $C_2H_5$. Other isocyanates may be prepared by processes illustrated in Scheme B.

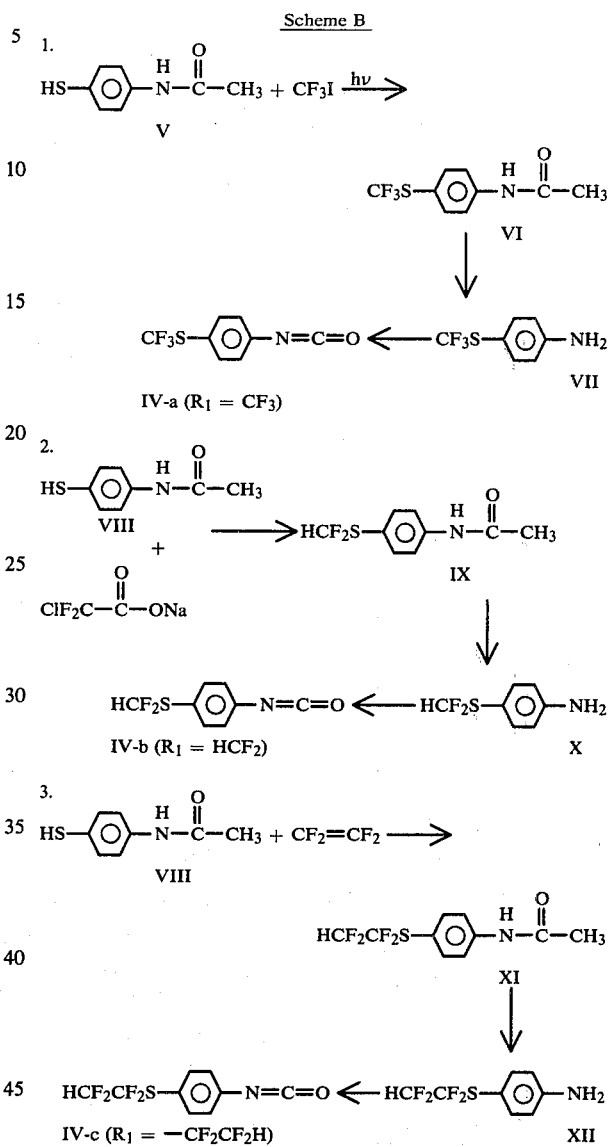

In reaction 1, p-acetamidothiophenol V is reacted with trifluoromethyl iodide in liquid ammonia under U.V. light at −33° C. When the reaction is complete, the ammonia is removed and water is added to the residue. The solid product VI is isolated by filtration and converted to the aniline VII by hydrolysis in alcoholic (ethanol or methanol) potassium or sodium hydroxide solution at a temperature of about 60°-80° C.

The product is isolated by diluting the reaction mixture with water and extracting with suitable solvent, such as ether or ethyl acetate. The aniline VII is then reacted with phosgene in a suitable solvent, such as toluene or xylene, at an initial temperature of about 40°-70° C. followed by heating to a temperature of about 100°-110° C. The product, isocyanate IV-a ($R_1$=$CF_3$), is isolated and purified by distillation.

In reaction 2, p-acetamidothiophenol VIII is contacted with alkaline salt (Na or Li) of chlorodifluoroacetic acid in 2-methoxyethyl ether as solvent at a temperature of about 130°-165° C., preferably 155°-165° C.

The resulting difluoromethyl adduct IX is converted to the isocyanate IV-b (R=HCF$_2$) through X in two steps, similar to the procedure described above.

In reaction 3, p-acetamidothiophenol VIII is reacted with tetrafluoroethylene in the presence of an organic base, for example, diisopropylamine. The reaction is carried out in a bomb in dimethylformamide or dimethylsulfoxide at a temperature in the range of about 0°–50° C., preferably between about 20°–30° C. The product is isolated by pouring the reaction mixture into water and extracting with ether. The resulting tetrafluoro derivative XI is converted to IV-c (R$_1$=—CF$_2$—CF$_2$H) through XII in two steps, similar to the procedure described above.

(b) Compounds of Formula I where X=OR$_2$

The esters of this invention, represented by Formula XIII,

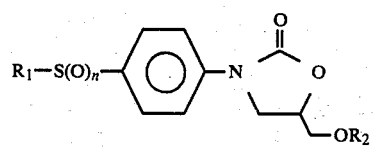

are prepared from key intermediates of Formulas XVI and XVII.

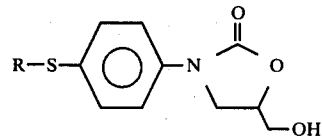

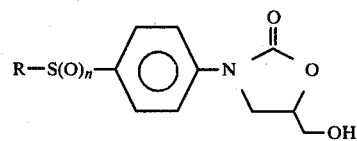

These intermediates may be prepared in a number of ways, as illustrated in Scheme C. The starting material for each of the processes in Scheme C is oxazolidinonemethyl halide II, prepared as described above.

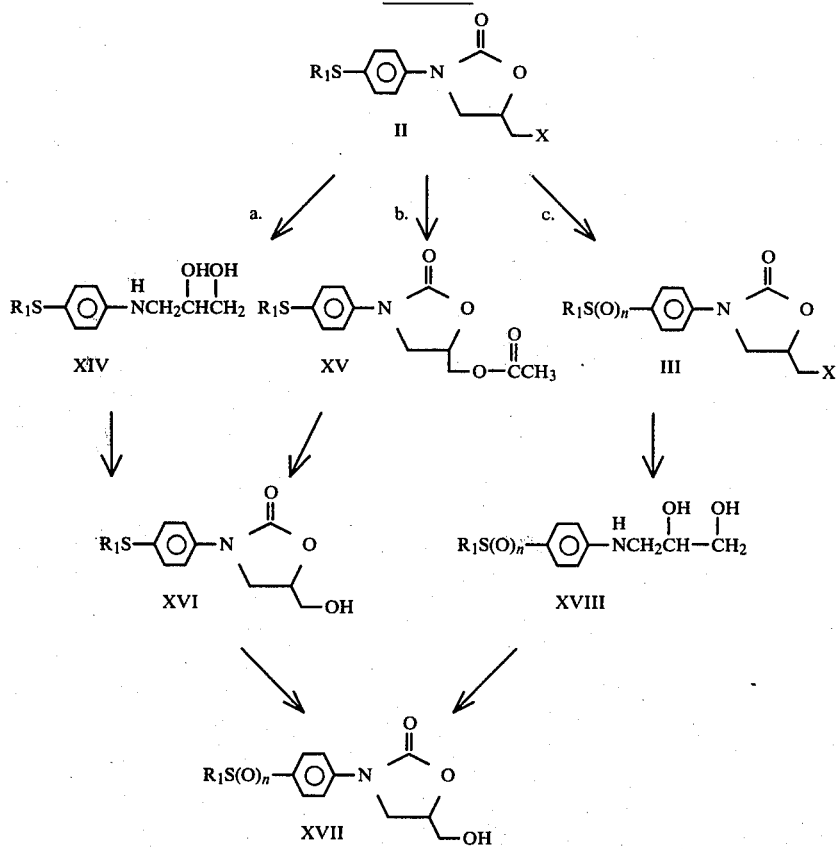

Reaction a involves the hydrolysis of II to the aminodiols XIV under basic conditions. The hydrolysis is best carried out in a water-alcohol (ethanol or methanol) solution of sodium or potassium hydroxide at a temperature in the range of about 40°–80° C., preferably between 70°–80° C. The product can be isolated by diluting the reaction mixture with water and extracting with methylene chloride. The resulting amino-diol XIV is then cyclized to XVI by reaction with diethyl or dimethyl carbonate in ethanol or 1,2-dimethoxyethane as solvent in the presence of a basic catalyst, for example, sodium ethoxide or methoxide. The product, which usually separates out as solid when the reaction mixture is cooled, is isolated by filtration.

Reaction b involves the displacement of X in II with carboxylate to give XV. This reaction is carried out with potassium acetate in dimethylformamide or dimethyl sulfoxide at a temperature in the range of about 80°–140° C., preferably between about 120°–130°. A catalyst such as 18-crown-6 can be used to facilitate reaction rate. The product is isolated by diluting the reaction mixture with water and extracting with a suitable solvent, for example, ether. The resulting ester XV is then converted to the methanol XVI under a basic hydrolysis condition. This reaction is carried out in alcoholic (methanol or ethanol) potassium or sodium hydroxide solution at a temperature in the range of about 0°–60° C., preferably between about 25°–30° C. The product, which usually separates out as solid when the reaction is complete, is isolated by filtration.

The method for the oxidation of the sulfide XVI to the corresponding sulfoxide XVII (n=1) or sulfone XVII (n=2) is the same as that for the oxidation of II or III described in Scheme A.

The product XVII can also be prepared from III via compound XVIII by a method analogous to that for the preparation of intermediate XVI from compound II via compound XIV.

The amino-diol intermediate XIV shown in Scheme C can be prepared by two alternate methods, illustrated by Scheme D.

diluting the reaction mixture with water and extracting with methylene chloride.

Various simple esters of XVI and XVII can be prepared as shown in Scheme D by reaction with the appropriate acid chloride or anhydride in an inert solvent, for example, methylene chloride, dimethylformamide, or 1,2-dimethoxyethane. The reaction is preferably run at a temperature in the range of about 0°–60° C., optionally in the presence of a base, for example, pyridine or triethylamine. When the anhydride reacted is cyclic such as succinic anhydride, the product is the succinic acid mono-ester XIII-a ($R_3$=—$CH_2$—$CH_2$—$CO_2H$).

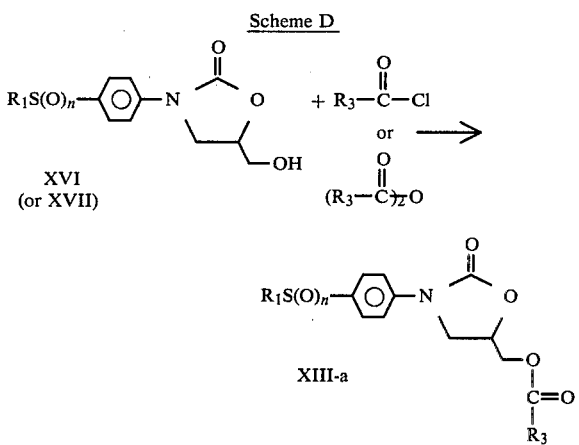

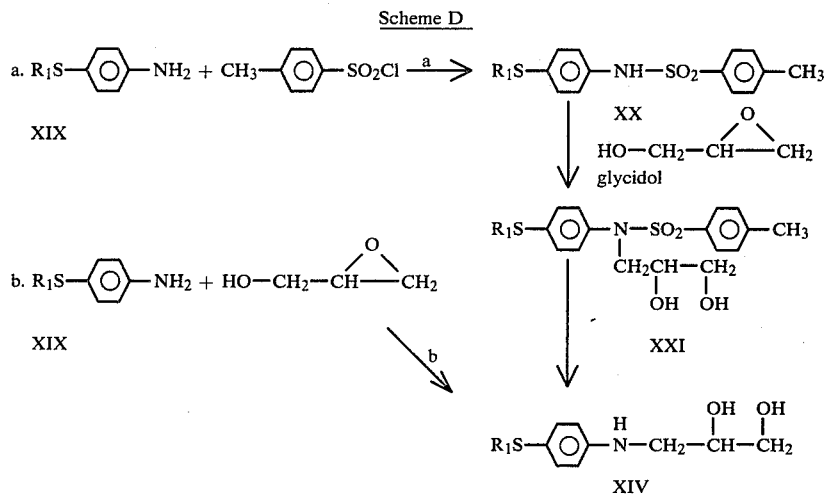

In reaction a, an aniline XIX is reacted with p-toluenesulfonyl chloride in a solvent such as tetrahydrofuran, 1,2-dimethoxyethane or acetonitrile in the presence of pyridine or aqueous sodium hydroxide. The reaction is carried out at a temperature in the range of about 0°–50°, preferably between about 20°–25°. The sulfonamide XX is then reacted with glycidol in the presence of a base, for example, 1,4-diazobicyclo[2,2,2-]=octane or triethylamine. Suitable solvents include dimethylformamide and dimethyl sulfoxide. The reaction is best carried out at a temperature in the range of about 80°–120° C., preferably between about 90°–100° C. The removal of the sulfonyl group in XXI is achieved by reacting XXI with naphthalene-sodium at a temperature in the range of about 10°–40° C., preferably between 25°–30° C. Suitable solvents include 1,2-dimethyloxyethane and tetrahydrofuran.

Alternatively, XIV may be obtained directly from the aniline XIX and glycidol in boiling methanol solution, as shown in reaction b. The product is isolated by Esters of XVI or XVII and amino acids are prepared, as shown in Scheme E, by condensation with N-protected amino acids XXII in the presence of condensing agent, for example, N,N-dicyclohexylcarbodiimide. Insert solvents such as methylene chloride or dimethylformamide are used, and the temperature used is in the range of about 0°–50° C., preferably between about 25°–40° C.

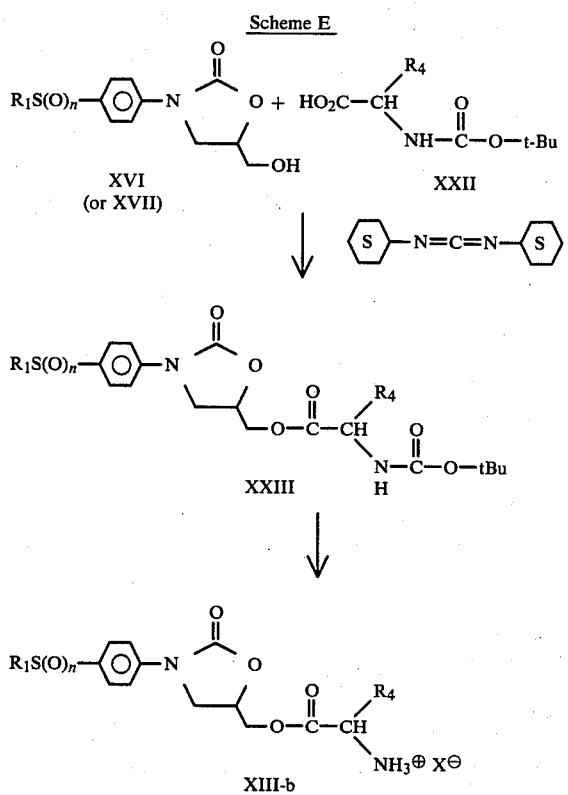

Scheme E

The product XXIII is isolated from the reaction mixture by removing the precipitated urea by filtration and concentrating the filtrate. The N-protecting group is then removed from XXIII by treatment with trifluoroacetic acid at a temperature in the range of about 0°–50° C., preferably between 5°–25° C. The product XIII-b is isolated by diluting the reaction mixture with ether and filtering the solid product.

(c) Optically active compounds

The product XVII (n=2), obtained by the methods described above, is a racemic mixture, that is, a 50:50 mixture of (+) and (−) enantiomers. The synthesis of optically active XVII ($R_1=CH_3$, n=2) can be achieved through resolution of the intermediate XIV, taking advantage of its basic nitrogen. Common resolving acids, for example, d or l-mandelic acid, can be used. Thus, XIV ($R_1=CH_3$) is reacted with l-mandelic acid in an aqueous ethanol solution. The resulting salt is then repeatedly recrystallized from acetonitrile until a constant melting point is obtained. The salt is then made basic by treatment with ammonium hydroxide to obtain the optically active (+)—XIV ($R_1=CH_3$). (+)—XIV is then converted to the optically active (−)—XVII ($R_1=CH_3$, n=2) by the route described previously. The (+)—XVII ($R_1=CH_3$, n=2) can also be prepared by using d-mandelic acid.

EXAMPLE 1

5-Chloromethyl-3-(4-methylthiophenyl)-2-oxazolidinone (II, $R_1=CH_3$, $X=Cl$)

To a hot (130° C.) solution of 105 g (0.64 mole) of 4-methylthiophenyl isocyanate and 93 g (1 mole) of epichlorohydrin in 600 ml of xylene was added 200 ml of tri-n-butylphosphine oxide-lithium bromide complex. (The complex was prepared by heating a mixture of 45 g of tri-n-butylphosphine oxide, 12.7 g of lithium bromide and 550 ml of xylene to reflux until a clear solution was obtained by removing water.) An exothermic reaction took place. After all of the catalyst had been added, the mixture was heated under reflux for 1 hour and cooled. The solution was decanted into a flask and concentrated to one-half the volume. An equal volume of petroleum ether was added to the residue. The solid that formed was collected by filtration and recrystallized from acetonitrile to give 102 g (62% yield) of the title compound; m.p. 106.5°–107.5° C.

EXAMPLE 2–4

By following procedures analogous to Example 1, the following compounds have been prepared:

| Example | Starting Materials (IV) | Products (II) |
| --- | --- | --- |
| 2 | 4-Trifluoromethylthiophenyl isocyanate | 5-Chloromethyl-3-(4-trifluoromethylthiophenyl)-2-oxazolidinone; m.p. 83–85° |
| 3 | 4-Difluoromethylthiophenyl isocyanate | 5-Chloromethyl-3-(4-difluoromethylthiophenyl)-2-oxazolidinone; m.p. 88–90° C. |
| 4 | 4-(1 1,2 2-Tetrafluoroethylthio)phenyl isocyanate | 5-Chloromethyl-3-[4-(1,1,2,2-tetrafluoroethylthio)phenyl]-2-oxazolidinone; m.p. 66–68° C. |

EXAMPLE 5

5-Chloromethyl-3-(4-trifluoromethylsulfonylphenyl)-2-oxazolidinone (III, R, $=CF_3$, $X=Cl$, n=2)

4.5 g (0.022 mole) of 85% m-chloroperbenzoic acid was added to a mixture of 2.9 g (0.01 mole) of 5-chloromethyl-3-(4-trifluoromethylthiophenyl)-2-oxazolidinone (II, $R_1=CF_3$, $X=Cl$) and 50 ml of methylene chloride. After the mixture was refluxed for 5 hours, the solvent was evaporated off by concentration, and the solid residue was triturated after ether and filtered to give 2.3 g of the title compound; m.p. 121°–123° C.

Anal. Calc'd for $C_{11}H_{10}ClF_3NO_4S$: C, 38.32; H, 2.92; N, 4.06, Found: C, 38.47; H, 2.72; N, 3.84.

EXAMPLE 6–8

By following procedures analogous to Example 5, the following compounds have been prepared:

| Example | Starting Material II | Product III |
| --- | --- | --- |
| 6 | 5-Chloromethyl-3-(4-difluoromethylthiophenyl)-2-oxazolidinone | 5-Chloromethyl-3-(4-difluoromethylsulfonylphenyl)-2-oxazolidinone; m.p. 127–129° C. Anal. Calc'd for $C_{11}H_{10}ClF_2NO_2S$. C, 40.56; H, 3.09; N, 4.30. Found: C, 40.61; H, 3.23; N, 4.17. |
| 7 | 5-Chloromethyl-3-[4-(1,1,2,2-tetrafluoroethylthio)phenyl]-2-oxazolidinone | 5-Chloromethyl-3-[4-(1,1,2,2-tetrafluoroethylsulfonyl)phenyl]-2-oxazolidinone; m.p. 123–125° C. Anal. Calc'd for $C_{12}H_{10}ClF_4NO_4S$: C, 38.36; H, 2.68; N, 3.73. Found: C, 38.39; H, 2.79; |

-continued

| Example | Starting Material II | Product III |
|---|---|---|
| 8 | 5-Chloromethyl-3-(4-methylthiophenyl)-2-oxazolidinone | N, 3.56.<br>5-Chloromethyl-3-(4-methylsulfonylphenyl)-2-oxazolidinone; m.p. 172–173° C. |

EXAMPLE 9

3-(4-Methylthioanilino)-1,2-propanediol (XIV, $R_1=CH_3$)

Method A

A mixture of 12 g of 4-methylthioaniline and 6.5 g of glycidol in 40 ml of methanol was heated under reflux for 2½ hrs. An additional 3 g of glycidol was introduced and the reflux was continued for an additional 2 hrs. To the cooled solution a mixture of 10 g of oxalic acid dissolved in 40–50 ml of warm methanol was added. The resulting solution was left sitting at room temperature and a solid product slowly separated out. After cooling in an ice-bath, the solid was collected by filtration. The oxalic acid salt was suspended on cold water and the mixture was made basic by adding 50% sodium hydroxide solution. The product that separated was extracted with methylene chloride. The extract was dried over anhydrous potassium carbonate, filtered, and concentrated to give an oily product which slowly solidified on standing. The solid was triturated with 1-chlorobutane, isolated by filtration, and dried at room temperature under a reduced pressure to give the 8.5 g of the title compound; m.p. 45°–46° C.

Method B

A mixture of 99 g of 5-chloromethyl-3-(4-methylthiophenyl-2-oxazolidinone, 34 g of sodium hydroxide, 300 ml of ethanol and 300 ml of water was heated under reflux for 5 hours. The mixture was concentrated to remove ethanol and the aqueous mixture was carefully made acidic by adding dilute hydrochloric acid. Some insoluble material was removed by filtration. The clear aqueous solution was then made basic by adding conc. ammonium hydroxide solution. The organic material was extracted with methylene chloride, and the methylene chloride extracts were dried over anhydrous potassium carbonate, filtered, and concentrated. The oily residue was treated with oxalic acid as in Method A to give the title compound; m.p. 45°–46° C.

Method C

A solution of 88 g (0.63 mole) of 4-methylthioaniline in 200 ml of 1,2-dimethoxyethane and 200 ml of water was stirred as a solution of 96 g of p-toluenesulfonyl chloride dissolved in 100 ml of 1,2-dimethoxyethane was added. During the addition, the solution was kept alkaline by the addition of 25% aqueous sodium hydroxide. The mixture was whipped-up well and base was added until the pH stayed 10–11. The mixture was made acid with conc. HCl and 1,2-dimethoxyethane was evaporated in a nitrogen stream. The solid was filtered and washed with water; yield 136.3 g; m.p. 103°–108° C. This product was recrystallized from 100 ml of acetonitrile to give 108.3 g; m.p. 108°–120° C. This was further purified by conversion to the sodium salt in 400 ml of 1,2-dimethoxyethane, using 26 g of 50% aqueous sodium hydroxide. The salt was filtered and washed with 1,2-dimethoxyethane. The solid was then resuspended in 500 ml of 1,2-dimethoxyethane and excess acetic acid, stirred, filtered and concentrated to yield 76.4 g of XX ($R_1=CH_3$); m.p. 110°–112° C.

A solution of 87.9 g of (0.3 mole) of this sulfonamide in 300 ml of dry DMF containing 5 g of 1,4-diazabicyclo[2.2.2]octane (DABCO) was heated at 100° C. under nitrogen. 22 g of glycidol (freshly distilled to remove polymer) in 25 ml of DMF was added over one hour. Heating was continued for three hours and a further 11 g of glycidol in 25 ml of DMF was added. One hour later the reaction mixture was poured into 2 l. of water which was allowed to stand overnight. The product had crystallized and was filtered and washed with water. The yield was 96 g; m.p. 97°–100° C. This was recrystallized from 150 ml of toluene to give 86.5 g of XXI ($R_1=CH_3$); m.p. 112°–113° C.

A solution of 450 g of naphthalene in 2 l. of 1,2-dimethoxyethane was stirred in a nitrogen atmosphere as 180 g of 40% sodium dispersed in mineral oil was added. The temperature was kept at 25°–30° C. by occasional cooling. After all of the sodium was added, stirring was continued for fifteen minutes. The solution (dark green to black) was then stirred as 213 g of the above tosylamide was added. The mixture was stirred for forty-five minutes. It remained black during this time, indicating an excess of the sodium naphthalene, radical anion. Water was added until the color had faded to yellow. Then, conc. hydrochloric acid was added until the solution had a pH=2–3. The 1,2-methoxyethane was removed by vacuum concentration. The water was extracted several times with hexane followed by toluene. The solution was sparged with nitrogen to remove the organic solvents and was then made alkyline with base (ammonium hydroxide) saturated with salt and extracted ten times with dichloromethane (or until no more organic base was obtained in the extract). The combined extracts were dried over anhydrous potassium carbonate, filtered and concentrated to give 131.4 g of the title compound, an oil which crystallized on standing; m.p. 45°–46° C.

EXAMPLE 10

By using the procedure analogous to Example 9, Method B, 3-(4-difluoromethylthioanilino)-1,2-propanediol (III, $R_1=CF_2H$) (m.p. 82°–84° C.) has been prepared from 5-chloromethyl-3-(4-difluoromethylthiophenyl)-2-oxazolidinone.

EXAMPLE 11

5-Hydroxymethyl-3-(4-methylthiophenyl)-2-oxazolidinone XVI, $R_1=CH_3$)

Method A

A mixture of 50 g (0.235 mole) of 3-(4-methylthioanilino)-1,2-propanediol (XIV, $R_1=CH_3$), 28 g (0.0237 mole) of diethyl carbonate, and 0.5 g of potassium t-butoxide in 200 ml ethanol was heated under reflux for 15 hours. An additional 7 g of diethyl carbonate and 0.7 g potassium t-butoxide were added and the reflux was continued for 3 hours. On cooling the solution, the solid product precipitated out, was collected by filtration and dried to give 50 g (89% yield) of the title compound; m.p. 135°–137° C.

Method B

A mixture of 15 g of II ($R_1=CH_3$, X=Cl), 50 g of potassium acetate, a catalytic amount of 18-crown-6, and 60 ml of dimethylformamide was heated under nitrogen atmosphere at 130° C. for 5 hours. The mixture was poured into ice water and the solid precipitate was collected by filtration. The solid was recrystallized from 1-chlorobutane to give 11 g of 5-acetoxymethyl-3-(4-methylthiophenyl)-2-oxazolidinone (XV, $R_1=CH_3$).

To a solution of 2.1 g of potassium hydroxide in 70 ml of methanol was added 10.4 g (0.037 mole) of the above compound XV ($R_1=CH_3$). The resulting solution was stirred at room temperature for three hours. An additional 0.2 g of potassium hydroxide was added and the stirring was continued for one hour. On cooling the solution, a solid precipitated. This solid was collected by filtration and washed well with cold methanol to yield 7.7 g (87% yield) of the title compound; m.p. 135°–137° C.

EXAMPLE 12

By following a procedure analogous to Example 11, Method A, the following compound has been prepared:

| Example | Starting Material (XIV) | Product XVI |
|---|---|---|
| 12 | 3-(4-Difluoromethylthio-anilino)-1,2-propanediol | 5-Hydroxymethyl-3-(4-difluoromethylthio-phenyl)-2-oxazolidinone; m.p. 120–122°. |

EXAMPLES 13–14

By following procedures analogous to Example 11, Method B, the following compounds have been prepared:

| Example | Starting Material (II) | Products (XVI) |
|---|---|---|
| 13 | 5-Chloromethyl-3-(4-trifluoromethylthio-phenyl)-2-oxazolidinone | 5-Hydroxymethyl-3-(4-trifluoromethylthio-phenyl)-2-oxazolidinone; m.p 142–143° C. |
| 14 | 5-Chloromethyl-3-[4-(1,1,2,2-tetrafluoro-ethylthio)phenyl]-2-oxazolidinone | 5-Hydroxymethyl-3-[4-(1,1,2,2-tetrafluoro-ethylthio)phenyl]-2-oxazolidinone; m.p. 134–136° C. |

EXAMPLE 15

5-Hydroxymethyl-3-(4-methylsulfonylphenyl)-2-oxazolidinone (XVII, $R_1=CH_3$, n=2)

To a solution of 50 g (0.21 mole) of 5-hydroxymethyl-3-(4-methylthiophenyl)-2-oxazolidinone (XVI, $R_1=CH_3$) in 600 ml of methylene chloride was added 93 g (0.46 mole) of 85% m-chloroperbenzoic acid in portions with cooling. The mixture was then stirred at room temperature for 15 hours. The resulting mixture was concentrated to remove methylene chloride and the solid residue was triturated with ether. The solid was collected by filtration and recrystallized from acetonitrile to give 48 g (85% yield) of the title compound; m.p. 177°–180° C.

EXAMPLE 16–18

By following procedures analogous to Example 15, the following compounds have been prepared:

| Example | Starting Materials (XVI) | Products (XVII) |
|---|---|---|
| 16 | 5-Hydroxymethyl-3-(4-trifluoromethylthio-phenyl)-2-oxazolidinone | 5-Hydroxymethyl-3-(4-trifluoromethylsulfonyl-phenyl)-2-oxazolidinone; m.p. 133–135° C. |
| 17 | 5-Hydroxymethyl-3-(4-difluoromethylthio-phenyl)-2-oxazolidinone | 5-Hydroxymethyl-3-(4-difluoromethylsulfonyl-phenyl)-2-oxazolidinone; m.p. 126–129° C. Anal. Calc'd for $C_{11}H_{10}F_3NO_5S$: C, 40.62; H, 3.10; N, 4.31. Found: C, 40.97; H, 3.30; N, 4.04. Anal. Calc'd for $C_{11}H_{11}F_2NO_5S$: C, 42.99; H, 3.61, N, 4.56. Found C, 43.16; H, 3.70; N, 4.91. |
| 18 | 5-Hydroxymethyl-3-[4-(1,1,2,2-tetrafluoro-ethylthio)phenyl]-2-oxazolidinone | 5-Hydroxymethyl-3-[4-(1,1,2,2-tetrafluoro-ethylsulfonyl)-phenyl]-2-oxazolidinone; m.p. 130–132° C. Anal. Calc'd for $C_{12}H_{11}F_4NO_5S$: C, 40.34; H, 3.10; N, 3.92. Found: C, 40.50; H, 3.18; N, 3.91. |

EXAMPLE 19

5-Hydroxymethyl-3-(4-methylsulfinylphenyl)-2-oxazolidinone (XVII, $R_1=CH_3$, n=1)

A mixture of 23.9 g (0.1 mole) of 5-hydroxymethyl-3-(4-methylthiophenyl)-2-oxazolidinone in 200 ml of dichloromethane was heated to reflux and stirred as 21.6 g of 80–90% m-chloroperoxybenzoic acid was added. Reflux was continued one hour. A thin layer showed that some starting compound remained, so an additional 5.3 g of 80–90% m-chloroperoxybenzoic acid was added and reflux was continued for eight hours. The resulting mixture was concentrated, stirred with ether, filtered and washed well with ether. The product was dissolved in water, potassium bicarbonate was added and the water was extracted with tetrahydrofuran. The extract was concentrated to yield 6.8 g.

This product was put through two silica gel columns on the Water's Prep 500 using a mixture of 70% dichloromethane and 30% acetonitrile. A broad peak was obtained but there was poor resolution of the two diastereoisomers. The six cuts were concentrated, and their melting points ranged from 143° C. to 153° C. All cuts appeared to have the same antibacterial activity.

The product is a mixture of the diasterioisomers of the title compound.

(dl)-3-(4-Methylsulfonylphenyl)-2-hydroxymethyl-2-oxazolidinone (XVII, $R_1=CH_3$, n=2)

A mixture of 60 g (0.207 mole) of 5-chloromethyl-3-(4-methylsulfonylphenyl)-2-oxazolidinone, 30 g of potassium hydroxide, 250 ml of water and 250 ml of ethanol was refluxed for two and one half hours. All solid dissolved. The solution was concentrated to remove the ethanol and was then made acid with hydrochloric acid. It was then made basic with ammonium hydroxide and concentrated to dryness. The solid was refluxed with tetrahydrofuran and filtered, and was then washed four times with tetrahydrofuran. The tetrahydrofuran extracts were combined and dried over anhydrous potassium carbonate and concentrated. The residue was dissolved in 133 ml of hot, absolute ethanol. The product crystallized, to give 39.3 g of XVIII ($R_1=CH_3$, $n=2$); m.p. 113°–114.5° C.

A mixture of 2.45 g (0.010 mole) of (dl)-3-(4-methylsulfonylanilino)-1, 2-propanediol in 20 ml of 1, 2-dimethoxyethane and 1.3 ml diethyl carbonate was heated to reflux under $N_2$ and 30 mg of sodium methoxide was added. The reaction was refluxed for two hours. The mixture was cooled to room temperature, and the solid was filtered and washed with ether followed by water. This yielded 2.4 g of the title compound; m.p. 176°–177° C.

EXAMPLE 21

4-Trifluoromethylthiophenyl Isocyanate (IV, $R_1=CF_3$)

To 250 ml of liquid ammonia was added 33 g (0.198 mole) of 4-acetamidothiophenol, followed by 42 g (0.214 mole) of trifluoromethyl iodide. The resulting mixture was stirred for 1 hr. at −33° C. under a U.V. sun lamp. The excess ammonia was evaporated off. Ice water was added to the solid residue after which the solid product was isolated by filtration. The product (VI), p-trifluoromethylthioacetanilide, was purified by recrystallization from acetonitrile; 44.3 g. (96% yield) obtained; m.p. 186°–7° C.

A mixture of 2.9 g of VI, 15 ml of ethanol and 2 g of potassium hydroxide was heated under reflux for four hours. The mixture was then concentrated to remove ethanol, and the residue was extracted with ether. The ether extract was dried over anhydrous potassium carbonate, filtered and concentrated to give the oily product VII, 4-trifluoromethylthioaniline. To a solution of 35 g of VII in 400 ml of toluene was rapidly added 25 ml of phosgene. The mixture was then stirred and slowly warmed to 70°∼80° C. When a homogeneous solution was obtained, the temperature was raised to 110° C. and held at that temperature for ½ hour. The solution was cooled and concentrated to give an oily product which was distilled to give 29 g (73% yield) of the title compound, 4-trifluorothiophenyl isocyanate; b.p. 39°–40° C./0.75. mm; IR max. 2300 $cm^{-1}$.

EXAMPLE 22

4-(1,1,2,2-Tetrafluoroethylthio)phenyl Isocyanate (IV, $R_1=-CF_2-CF_2H$)

A mixture of 25 g (0.15 mole) of 4-acetamidothiophenol and 15 g (0.15 mole) of diisopropylamine in 80 of dimethylformamide was treated with 15 g (0.15 mole) of tetrafluoroethylene in a bomb. The temperature was slowly raised from −44° C. to 25° C. The reaction mixture was then poured into water and the solid product was isolated by filtration. The solid was dissolved in ethyl acetate and the resulting solution was dried over anhydrous magnesium sulfate, filtered, and concentrated. The solid residue was triturated with petroleum ether and filtered to give 35 g (87.5% yield) of p-(1,1,2,2-tetrafluoroethylthio)acetanilide (XI); m.p. 133.5°–135° C.

A mixture of 5 g of XI and 40 ml of 6 N hydrochloric acid was heated under reflux for 4 hours. The mixture was diluted with 200 ml of water and filtered. The filtrate was concentrated to dryness and the solid residue was triturated with ether and filtered to give 4-(1,1,2,2-tetrafluoroethylthio)aniline (XII) as a hydrochloride salt.

XII was reacted with phogene as in Example 21 to give the title compound, 4-(1,1,2,2-tetrafluoroethylthio)phenyl isocyanate; b.p. 73° C./25 mm., IR max. 2270 $cm^{-1}$.

EXAMPLE 23

4-Difluoromethylthiophenyl Isocyanate (IV, $R_1=HCF_2$)

Over the period of one hour, 5.5 g (0.04 mole) of lithium chlorodifluoroacetate dissolved in 20 ml of 2-methoxyethyl ether was added to a stirred solution of 3.4 g (0.02 mole) of 4-acetamidothiophenol and 0.2 g of potassium t-butoxide in 30 ml of 2-methoxyethyl ether at 140° C. The resulting mixture was then heated at 140° C. for 10 minutes and poured into ice water. The cold mixture was made basic with dilute sodium hydroxide solution and filtered. The solid was dissolved in ethyl acetate. The ethyl acetate solution was washed with dilute sodium hydroxide solution and saturated sodium chloride solution, dried, filtered, and concentrated to yield 3.5 g of the product p-difluoromethylthioacetanilide (IX); m.p. 141°–3° C.

A mixture of 71 g (0.33 mole) of IX, 45 g of potassium hydroxide, and 300 ml of methanol was heated under reflux for 15 hours. The mixture was concentrated to remove methanol and the residue was diluted with water. The organic material was extracted with ether and the ether extract was dried over anhydrous magnesium sulfate, filtered, and concentrated. The liquid residue was distilled to give pure 4-difluoromethylthioaniline (X); b.p. 70°–75° C./0.15 mm.

X (5 g.) was reacted with 30 ml of phosgene as in Example 21 to give 4.4 g (77% yield) of the title compound, 4-difluoromethylthiophenyl isocyanate; b.p. 75°–79° C./0.25 mm., IR max. 2250 $cm^{-1}$.

EXAMPLE 24

(dl)-3-(4-Methylsulfonylphenyl)-2-oxooxazolidin-5-ylmethyl 1,4-Butanedioic Acid Mono Ester, Mono Sodium Salt A solution of 22 g (0.081 mole) of 3-(4-methylsulfonylphenyl)-5-hydroxymethyl-2-oxazolidinone in 110 ml of pyridine was stirred while 8.5 g of succinic anhydride was added. The solution was kept at 50° C. for two hours. Crystals separated on standing. The mixture was poured into water, and hydrochloric acid was added until the pH was 1 or lower. The product was filtered and washed with water. The yield was 24.2 g; m.p. 159°–162° C. This was recrystallized from nitromethane to give 22.6 g; m.p. 167°–168° C.

A suspension of 22.3 g of this acid 250 ml of distilled water was stirred and solid sodium bicarbonate was added until all of the solid acid had dissolved and the pH was 8.3. The solution was filtered through Celite Analytical Filter Aid. The solution was vacuum concentrated and ethyl alcohol was added and removed under vacuum. Xylene was added and removed under reduced pressure. The solid was slurried with xylene, filtered and washed with ether to give 32 g of the title product as a mono hydrate.

EXAMPLE 25

5-L-Alanyloxymethyl-3-(4-methylsulfonyl)phenyl-2-oxazolidinone Trifluoroacetic Acid Salt (XIII-b, $R_1=CH_3$, $n=2$, $R_4=CH_3$, $X=CF_3CO_2$)

A solution of 4.5 g (0.02 mole) of N,N'-¹dicyclohexylcarbodiimide in methylene chloride was added to a solution of 5.4 g (0.02 mole) of 5-hydroxymethyl-3-(4- methylsulfonylphenyl)-2-oxazolidinone, 3.8 g (0.02 mole) of N-t-butyloxycarbonyl-L-alanine, 1.2 g of pyridine and 100 ml of methylene chloride. The resulting mixture was stirred at room temperature for 18 hours after which the solid precipitate was removed by filtration. The filtrate was successively washed with 1 M potassium bisulfate, water, and dilute sodium bicarbonate, and was dried over anhydrous magnesium sulfate and concentrated. The solid residue was recrystallized from ethyl acetate to give XXIII ($R_1=CH_3$, n=2, $R_4=CH_3$).

2.2 g. of XXIII was added to 15 ml of cold (0° C.) trifluoroacetic acid. After stirring at 0° C. for 15 minutes, the solution was poured into ether. The solid precipitate was collected by filtration and dried to yield the title compound.

EXAMPLE 26

1-3-(4-Methylsulfonylphenyl)-2-oxooxazolidin-5-ylmethyl n-Heptanoic Acid Ester

To a solution of 1.3 g of l-isomer of XVII ($R_1=CH_3$, n=2) (from Example 27) and 0.6 g of triethylamine in 20 ml of 1,2-dimethoxyethane was added at 0° C. a solution of 0.8 g of n-heptanoyl chloride in 10 ml of 1,2-dimethoxyethane. After 1½ hours of stirring, additional 0.3 g of n-heptanoyl chloride was added. After one hour of stirring at room temperature, the mixture was poured into water and the solid product was isolated by filtration. The solid was recrystallized from ethanol to give 1.6 g of the title compound; m.p. 138°–140° C.

Anal. Calc'd for: $C_{18}H_{25}NO_6S$; C, 56.4; H, 6.6; N. 3.7. Found: C, 57.0; H, 6.8; N, 3.7.

EXAMPLE 27

R-(−)-3-(4-Methylsulfonylphenyl)-5-hydroxymethyl-2-oxazolidinone

A mixture of 148.5 g of (dl)-3-(4-methylthioanilino)-1,2-propanediol, 570 ml of 20% ethanol-80% water and 110 g of l-mandelic acid was stirred and warmed untill all solid dissolved. On standing and cooling, crystals separated. These were filtered and washed with 20% ethanol and water and dried; yield 83 g; m.p. 99.5°–100.5° C. The product was recrystallized from 350 ml acetonitrile yielding 76 g; m.p. 101°–101.6° C. Recrystallizing this from 320 ml of acetonitrile containing 3 g of l-mandelic acid gave 64.0 g; m.p. 101°–102.0° C.

A 63.4 g portion of the above l-mandelic acid salt was suspended in 100 ml of water, 100 ml of chloroform was added, and ammonium hydroxide was added until strongly basic. The amine was extracted into the chloroform layer which was separated. The water layer was extracted four times with 25 ml portions of chloroform. The combined chloroform extracts were dried over anhydrous potassium carbonate, filtered and concentrated to give 41.3 g of oil. The oil was dissolved in 50 ml of dichloromethane and was allowed to stand overnight. The product crystallized; this was filtered and washed with dichloromethane: yield 35.4 g; m.p. 68°–69° C. (One sample obtained at this stage melted 76.5°–78° C.) This product is:

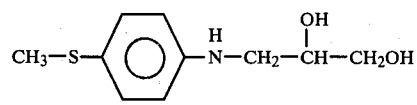

$[\alpha]_D = 21.2 \pm 0.5°$
(C = 1 in ethanol)

A solution of 35.4 g (0.166 mole) of (d)-3-(4-methylthio)anilino-1,2-propanediol in 140 ml of 1,2-dimethoxyethane and 21 ml of diethyl carbonate was heated to reflux and stirred as 0.1 g of sodium methoxide was added. The mixture was refluxed two hours and then cooled to room temperature. The product crystallized. The suspension was stirred and acetic acid (a few drops) was added until a portion diluted with water was no longer basic. The product was filtered and washed with 1-propanol, then dried to yield 28.9 g; m.p. 138°–139° C. The product was recrystallized from acetonitrile, filtered hot, to give 26.4 g; m.p. 139°–140° C. The product of this reaction is:

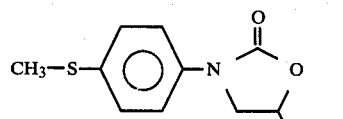

$[\alpha]_D = -66.5 \pm 0.5°$
(C = 0.9 in acetonitrile)

A solution of 26.1 g (0.109 mole) of 3-(4-methylthiophenyl)-5-hydroxymethyl-2-oxazolidinone in 600 ml of dichloromethane was heated to reflux. The heat source was then removed and 55 g of m-chloroperoxybenzoic acid was added at a rate allowing for smooth refluxing. At the end of the addition, the mixture was refluxed one-half hour. The excess peracid was destroyed by slowly adding 7 ml of methyl sulfide and refluxing ten minutes. At this stage a test for excess per acid was negative. The resulting mixture was concentrated under reduced pressure and the solid was stirred with 500 ml of ether for two hours then filtered and washed five times with 100 ml portions of ether. The dried yield was 29.1 g; m.p. 183°–184° C. This was recrystallized from 275 ml of acetonitrile to give 22.6 g; m.p. 183°–184° C. A final recrystallization from 250 ml. of acetonitrile, filtering hot, gave 17.6 g; m.p. 188°–189° C. and a second crop of 3.3 g; m.p. 187.5°–188° C. was obtained. These two crops were blended together to give 20.8 g; m.p. 188.5°–190° C. The product is:

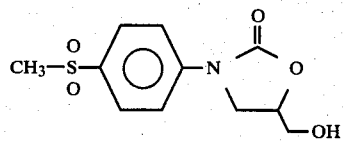

$[\alpha]_D = -61.9 \pm 0.1°$
(C=0.884 in acetonitrile)
Anal. Calcd. for $C_{11}H_{13}NO_5S$: C, 48.70; H, 4.83; N, 5.16. Found: C, 48.74, 48.71; H, 4.93, 4.82 N, 5.19, 5.07.

EXAMPLE 28

1-3-(4-Methylsulfonylphenyl)-2-oxooxazolidin-5-ylmethyl 1,4-Butanediodic Acid Mono Ester, Mono Sodium Salt A mixture of 5.0 g (0.0184 mole) of 1-3-(4-methylsulfonylphenyl)-5-hydroxymethyl-2-oxazolidinone in 110 ml of pyridine was stirred and 2.1 g of succinic anhydride was added. The solution was kept at 50° C. for four hours, cooled and poured into 300 ml of water and made acid with conc. hydrochloric acid. The product was filtered, washed with water and dried; yield 4.32 g; m.p. 155°–160° C. This was recrystallized from 20 ml of nitromethane to give 3.48 g; m.p. 163°–164.2° C.

A 3.042 g portion was suspended in 50 ml of water; a small amount of ethanol was added to assist wetting and 1 N sodium hydroxide was added until the pH was 7.5. The water solution was concentrated to give 3.21 g of white solid.

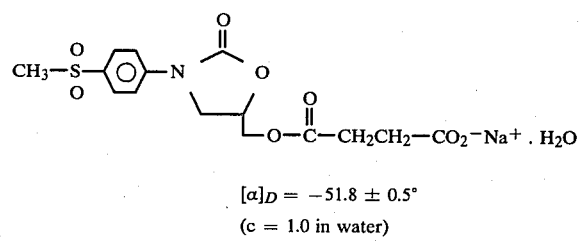

$[\alpha]_D = -51.8 \pm 0.5°$
(c = 1.0 in water)

Dosage Forms:

The antibacterial agents of this invention can be administered by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characterisitcs of the particular agent, and its mode and route of administration; age, health and weight of the recipient; nature and extent of symptoms, kind of concurrent treatment, frequency of treatment, and the effect desired. Usually a daily oral dosage of active ingredient can be about 10 to 20 milligrams per kilogram of body weight. Ordinarily, when the more potent compounds of this invention are used, 5 to 15 and preferably 5 to 7.5 milligrams per kilogram per day, given in divided doses 2 to 4 times a day or in sustained release form, is effective to obtain desired results. These drugs may also be administered parenterally.

Dosage forms (compositions) suitable for internal administration contain from about 1.0 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets and powders, or in liquid dosage forms, such as elixirs, syrups and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coating for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfate, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propylparaben and chlorobutanol.

Suitable pharmaceutical carriers are described in Remington's Pharmaceutical Sciences, E. W. Martin, a standard reference text in this field.

Useful pharmaceutical dosage forms for administration of the compounds of this invention can be illustrated as follows:

Capsules

A large number of unit capsules are prepared by filling standard two-piece hard gelatin capsules each with 50 milligrams of powdered active ingredient, 175 milligrams of lactose, 24 milligrams of talc and 6 milligrams magnesium stearate.

A mixture of active ingredient in soybean oil is prepared and injected by means of a positive displacement pump into gelatin to form soft gelatin capsules containing 50 milligrams of the active ingredient. The capsules are washed in petroleum ether and dried.

Tablets

A large number of tablets are prepared by conventional procedures so that the dosage unit is milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 milliliters contain 10 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

Utility:

This class of novel chemical compounds is active, in-vitro, against a wide variety of bacterial organisms including the gram negative enterobacteriaceae; beta-lactamase-producing staphylococci, and anaerobic bacteria. These microorganisms are of major human and veterinary medical importance as the recognized causative agents of infections involving the blood; central nervous system; respiratory system, gastro-intestinal system; genito-urinary tract, interstitial fluids, soft tissue and bone.

The compounds listed below in Table 1 were tested for in vivo and in vitro antibacterial activity. The twenty-four hour minimum inhibitory in vitro concentrations (MIC) for a test strain of Staphylococcus epidermidis of the compounds were determined using a standard microdilution method with Mueller-Hinton broth. This method is described in Conrath, Theodore B., 1972 Handbook of Microtiter Procedures, Dynatech Corporation, Cambridge, Mass., the disclosure of which is herein incorporated by reference.

The in vivo antibacterial activity of the compounds was determined as follows.

Cultures of Staphylococcus aureus or Escherichia coli were grown from stored frozen stocks in trypticase soy broth (BBL), a standard bacteriological growth medium, with shaking until a turbidity of optical density ($650\mu$) of 0.4–0.5 was attained. These cultures were centrifuged and resuspended in either 50% hog gastric mucin for Staphyloccus aureus or saline for Escherichia coli. These suspensions were injected intraperitoneally at dilutions calculated to cause 90–100% mortality within 7 days of the mice of the control groups.

The compounds were suspended or dissolved in 0.25% Methocel, 15 CPS, at various concentrations. Mice were dosed orally by intubation at the time of infection and again four hours later. Mortality was recorded daily until test termination. The estimated dose 50 (ED50) was calculated by the Reed-Muench method, as described in Reed, L. J. and Muench, H., American Journal of Hygiene, 27, 493–497 (1938), the disclosure of which is herein incorporated by reference.

TABLE 1

Antibacterial Activity of 2-oxazolidinone derivatives

| Compound | In-Vitro[1] MIC; μg/ml | In-Vivo S. aureus | ED$_{50}$; mg/kg E. coli |
|---|---|---|---|
| 5-chloromethyl-3-(4-methylsulfinyl)phenyl-2-oxazolidinone | 25 | — | — |
| 5-chloromethyl-3-(4-methylsulfonyl)phenyl-2-oxazolidinone | 5 | 29 | 63 |
| 5-Fluoromethyl-3-(4-methylsulfonyl)phenyl-2-oxazolidinone | 20 | 35 | — |
| 5-Bromomethyl-3-(4-methylsulfonyl)phenyl-2-oxazolidinone | 5 | — | — |
| 5-Hydroxymethyl-3-(4-methylsulfinyl)phenyl-2-oxazolidinone | 50 | 27 | — |
| 5-Hydroxymethyl-3-(4-methylsulfonyl)phenyl-2-oxazolidinone | 12.5 | 18 | 40 |
| (1)-5-Hydroxymethyl-3-(4-methylsulfonyl)phenyl-2-oxazolidinone | 12.5 | 9 | 25 |
| 5-Acetoxymethyl-3-(4-methylsulfonyl)phenyl-2-oxazolidinone | >50 | 100 | — |
| (dl)-mono-{3-[4-(methylsulfonyl)phenyl]-2-oxooxazolidin-5-ylmethyl} butanedioic acid ester, monosodium salt | >50 | 26 | 40 |
| (l)-mono{3-[4-(methylsulfonyl)phenyl]-2-oxooxazolidin-5-ylmethyl} butanedioic acid ester, monosodium salt | — | 20 | — |
| 5-(L)-Alanyloxymethyl-(1)-3-(4-methylsulfonyl)phenyl-2-oxazolidinone trifluoroacetic acid salt | 25 | 14 | — |
| 5-chloromethyl-3-(4-ethylsulfonyl)phenyl-2-oxazolidinone | 50 | — | — |
| 5-chloromethyl-3-(4-difluoromethylsulfonyl)phenyl-2-oxazolidinone | 2.5 | 20 | — |
| 3-(4-Difluoromethylsulfonyl)phenyl-5-hydroxymethyl-2-oxazolidinone | 3.1 | 23 | 27 |
| 5-Chloromethyl-3-(4-trifluoromethylsulfonyl)phenyl-2-oxazolidinone | 4.7 | 105 | — |
| 5-Hydroxymethyl-3-(4-trifluoromethylsulfonyl)phenyl-2-oxazolidinone | 12.5 | 20 | — |
| 5-Chloromethyl-3-[4-(1,1,2,2-tetrafluoroethylsulfonyl)phenyl]-2-oxazolidinone | 10 | 92 | — |
| 5-Hydroxymethyl-3-[4-(1,1,2,2-tetrafluoroethylsulfonyl)- | | | |

TABLE 1-continued

| | Antibacterial Activity of 2-oxazolidinone derivatives | | |
|---|---|---|---|
| Compound | In-Vitro[1] MIC; μg/ml | In-Vivo S. aureus | ED$_{50}$; mg/kg E. coli |
| phenyl]-2-oxazolidinone | 12.5 | 108 | — |

[1]24-Hour minimum inhibitory concentration: determined by microdilution method with *S. epidermidis* as the test organism.

The in-vitro antibacterial activity spectrum of (1)-5-Hydroxymethyl-3-(4-methylsulfonyl)phenyl-2-oxazolidinone, determined by an agar dilution procedure, is shown in table 2. This procedure is known in the art and can be summarized as follows. Petri plates were prepared containing two-fold compound concentrations, ranging from 1.0 μg/ml to 128 μg/ml, incorporated into Mueller-Hinton agar. The agar plates were inoculated with a 0.001 ml calibrated loopful of bacterial inoculum diluted to contain $5 \times 10^6$ colony forming units (CFU) per ml. The MIC was recorded as the lowest compound concentration which inhibited macroscopic bacterial growth during a 24-hour incubation period at 35° C. The test organisms included clinical bacterial isolates representing two gram positive and nine gram negative genera.

TABLE 2

In-Vitro Susceptibility of Clinical Bacterial Isolates to (1)-5-hydroxymethyl-3-(4-methylsulfonyl)phenyl-2-oxazolidinone

| Test Organism | No. Isolates | Mean MIC[1] μg/ml |
|---|---|---|
| Serratia sp. | 44 | ≧108.4 |
| Enterobacter sp. | 41 | 37.9 |
| E. coli | 86 | 21.7 |
| Proteus sp. | 88 | 21.7 |
| Pseudomonas sp. | 78 | ≧128.0 |
| Salmonella sp. | 6 | 16.0 |
| Shigella sp. | 9 | 11.6 |
| Staphylococci sp. | 37 | 3.8 |
| Klebsiella sp. | 68 | 37.5 |
| Providencia sp. | 12 | 26.7 |
| Streptococci sp. | 12 | 3.7 |
| Neisseria sp. | 42 | 10.5 |
| *Hemophilus influenzae* | 4 | 16 |

[1]MIC: Minimum Inhibitory Concentration determined by agar dilution

The inhibitory activity for anaerobic bacteria of 5-chloromethyl-3-(4-difluoromethylsulfonyl)phenyl-2-oxazolidinone and (1)-5-hydroxymethyl-3-(4-methylsulfonyl)phenyl-2-oxazolidinone was determined using the agar dilution method described in Barry, Arthur L., The Antimicrobic Susceptibility Test: Principles and Practices, 1976 Lea & Febiger, Philadelphia. The minimum inhibitory concentrations, as shown in Table 3, indicate that these compounds are potent inhibitors of anaerobic bacterial growth.

TABLE 3

In-vitro Susceptibility of Anaerobic Clinical Bacterial Isolates

| | 5-chloromethyl-3-(4-difluoromethyl-sulfonyl)-phenyl-2-oxazolidinone | | (1)-5-Hydroxymethyl-3-(4-methylsulfonyl)-phenyl-2-oxazolidinone | |
|---|---|---|---|---|
| Test Organism | No. Isolates Tested | Mean MIC[1] μg/ml | No. Isolates Tested | Mean MIC μg/ml |
| Clostridium sp. | 4 | 1.0 | 4 | 7.0 |
| Fusobacterium sp. | 4 | 0.06 | 4 | 0.3 |
| Bacteroides sp. | 32 | 1.8 | 28 | 3.4 |
| Gram positive cocci | 7 | 0.7 | 7 | 1.3 |

[1]48-hour minimum inhibitory concentration determined by agar dilution

What is claimed is:

1. A compound of the formula:

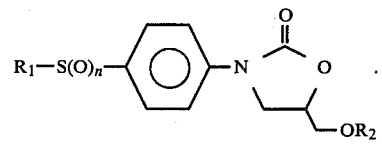

where
$R_1 = CH_3, C_2H_5, CF_2H, CF_3$ or $CF_2CF_2H$;

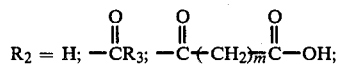

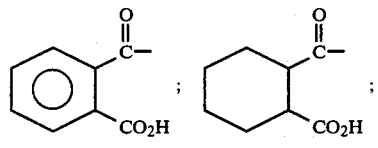

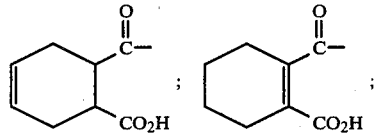

or

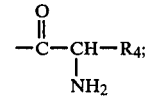

$R_3$ = aryl or $C_1$-$C_{12}$ alkyl;
$R_4$ = H, $C_1$-$C_5$ alkyl, —CH$_2$OH, —CH$_2$SH, aryl or aralkyl;
n = 1 or 2; and
m = 2 or 3;
and pharmaceutically acceptable acid and base salts thereof.

2. A compound of claim 1 wherein $R_2$ = H or

3. A compound of claim 1 where n=2.

4. A compound of claim 1 where $R_2$=H or —$COR_3$ and n=2.

5. A pharmaceutical composition consisting essentially of a suitable pharmaceutical carrier and an effective antibacterial amount of a compound of claims 1 to 4.

6. A method for alleviating bacterial infection in a mammal which comprises administering to the mammal an effective antibacterial amount of a compound of the formula:

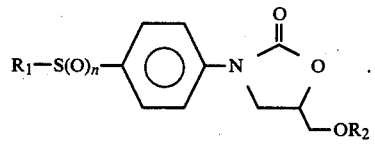

where
$R_1$—$CH_3$, $C_2H_5$, $CF_2H$, $CF_3$ or $CF_2CF_2H$;

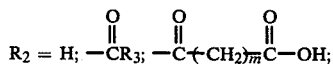

-continued

[structures shown]

or

[structure with —C(O)—CH(NH₂)—R₄]

$R_3$=aryl or $C_1$-$C_{12}$ alkyl;
$R_4$=H, $C_1$-$C_5$ alkyl, —$CH_2OH$, —$CH_2SH$, aryl or aralkyl;
n=1 or 2; and
m=2 or 3;
and pharmaceutically acceptable acid and base salts thereof.

7. The method of claim 6 wherein $R_2$—H or $-\overset{O}{\underset{\|}{C}}R_3.$ 8. The method of claim 6 wherein $R_2$=H or $COR_3$ and n=2.

* * * * *